United States Patent [19]

Crivella et al.

[11] Patent Number: 4,650,109

[45] Date of Patent: Mar. 17, 1987

[54] METHOD OF MANUFACTURE OF BONE IMPLANT POROUS SURFACES

[76] Inventors: Charles Crivella, 14643 Murthum, Warren, Mich. 48093; Lee A. Stouse, 2661 Canfield Trail, Brighton, Mich. 48116

[21] Appl. No.: 690,996

[22] Filed: Jan. 14, 1985

[51] Int. Cl.$^4$ .......................... B23K 29/00; C22C 9/00
[52] U.S. Cl. ..................................... 228/194; 228/195; 228/263.21; 420/489; 420/492; 128/92Y G; 623/18; 623/22
[58] Field of Search ............ 228/194, 195, 198, 263.21; 420/451, 489, 492; 128/92 G, 92 C; 623/18, 22, 23

[56] References Cited

U.S. PATENT DOCUMENTS

| | | | |
|---|---|---|---|
| 3,034,205 | 5/1962 | Ames | 228/263.12 |
| 3,561,099 | 2/1971 | Mizuhara | 228/263.21 |
| 3,591,917 | 7/1971 | Shira | 228/263.21 |
| 3,981,429 | 9/1976 | Parker | 228/263.21 |
| 4,034,906 | 7/1977 | Carlson et al. | 228/263.21 |
| 4,357,299 | 11/1982 | Pattanaik | 420/489 |
| 4,493,736 | 1/1985 | Adams | 420/489 |

OTHER PUBLICATIONS

Bulletin of Alloy Phase Diagrams, vol. 2, No. 2, 1981, pp. 169, 170, American Society for Metals.
Technology in Orthopaedics, "Morphology of Porous Surfaces".

Primary Examiner—Nicholas P. Godici
Assistant Examiner—Samuel M. Heinrich
Attorney, Agent, or Firm—Burton, Parker & Schramm

[57] ABSTRACT

Described is a method of manufacture of bond implant so to create a porous surface. The bone implant is made of titanium or titanium alloy. The porous surfaces are attached to a titanium substrate by use of a joinder agent including copper, nickel and indium, which is heated to temperatures less than the beta transus.

7 Claims, No Drawings

METHOD OF MANUFACTURE OF BONE IMPLANT POROUS SURFACES

DESCRIPTION

1. Field of Invention

The present invention relates generally to prosthetic parts, particularly dealing with devices to be used as high strength artificial bone implants made of titanium to insure a strong union with the bone matter into which the device is implanted. Specifically, it deals with use of a compound in manufacturing such a device.

2. Background of the Invention

Starting in the late sixties there was developed a new method for making bone implants so they would better join to the bones with which they were to be attached. This method was described by, among others, Hahn in his U.S. Pat. No. 3,605,123, and Pilliar in his U.S. Pat. No. 3,855,638. These implants consisted of a metal core upon which was placed a porous surface into which bone could grow to provide a fixed implant. Several methods have developed as being of most interest. One is plasma flame spray wherein molten metal is impinged upon the substrate to create a surface of interconnected peaks and valleys to the bone may grow. Because of the nature of the process, variations in the surface porosity are expected in this type of process. Alternative methods to give more uniform porosity include the placement of uniform spherical beads in a generally consistent organized arrangement of pores. The pore size of such a surface is a function of the bead diameter and is approximately one-third the bead diameter. The shape of the pores depends upon how the beads are packed together and the necking which occurs between the beads after the process which joins them to the substrate. Another method currently being used is the use of fiber metal pads which are created by compaction and diffusion bonding of randomly oriented wires, typically titanium, for use on a titanium base. Like the beads, they are then joined to the substrate. Titanium alloys such as titanium—6% aluminum—4% vanadium, have been found to be one of the most durable implant materials now available. Unfortunately, the current methods of joining the porous surface to the implant substrate normally requires the heating of the titanium alloy to high temperatures, much higher than titanium's beta transus point. In such a case, the structure of the titanium changes from a hexagonal close-packed crystalline structure or alpha phase to a body centered cubic crystal, the high temperature or beta phase. In passing the beta transus, the strength of the titanium alloy is greatly diminished and therefore use of titanium implants has been, until now, restricted to those body implants which do not require great strength. In high strength areas, such as hip bone replacement, cobalt steel is often used, which, unfortunately, has almost twice the weight of the titanium or its alloy mentioned above. It is the purpose of this invention to avoid the need to pass the beta transus and therefore allow the use of titanium in areas for bone implants currently not available to it, and thus make for lighter implants.

SUMMARY OF THE INVENTION

This invention relates to the use of bone implants having a porous surface such as a spherical bead or fiber metal pad surface where it is to be joined with the bone. It provides a method wherein the beads or metal pads can be attached to the titanium substrate without a need to pass over the beta transis and thereby maintain the stronger hexagonal close packed crystalline structure to the titanium. This is done by using an activator compound in the form of a powder which is a combination of copper, nickel, and indium. This combination reacts with the titanium in the substrate and the beads or metal pads to be attached so to join the elements into an implant stronger than the surrounding bone.

DETAILED DESCRIPTION OF THE INVENTION

The invention provides for an implant substrate corresponding to the bone element to be replaced. Along a surface of the substrate corresponding to where the substrate will be joined with the patient's bone, there is placed porous means which, when joined to the substrate, will create a porous surface into which the adjoining bone may grow. These porous means may be in the form of uniform spherical beads or porous titanium fiber metal pads. In either case, for purposes of this invention there should be in essence a plurality of small particles of titanium and/or titanium alloy so that when bonded together at their points of contact they will define a plurality of connected interstitial pores along their surface.

Pursuant to the invention, a joinder compound comprising a powder in the form of copper, nickel and indium is applied to the substrate to which the porous means is to be attached. This can be done in any number of ways, such as coating the substrate with an aqueous solution with organic binders and sprinkling, spraying, or transfer tape application. Porous means are then applied to the substrate over the joining compound. This can be repeated as often as necessary to develop the required thickness of the porous coating. The implants are then allowed to dry and then can be inspected for uniformity and completeness of coverage. The implants are then placed in a furnace having a nonreactive atmosphere, for example, a vacuum, argon, or helium atmosphere. They are then heated until the joining compounds melts. This will occur below the beta transus of the titanium or titanium alloys used, and will provide an implant that can now be precipitation heat treated or age hardened to increase the substrate strength due to the presence of an alpha structure.

A specific example used by the inventors has been creating a titanium alloy substrate of titanium—6% aluminum—4% vanadium, and placing over it a joinder compound comprised of 63% to 66% copper, 30 to 36% nickel, 3% to 5% indium and up to 5% titanium of not more than 1% iron and other impurities, and then placing titanium alloy spheres over the substrate will provide a basis for a bone implant which when heated to less than the beta transus will provide the advantages desired. The inventors have proceeded to bind the beads and substrate together by placing the implant in a furnace where a vacuum is created of $1 \times 10^{-4}$ torr, and then heating the temperature within the furnace at 50° F. per minute to 1000° F., all the time maintaining a vacuum of $5 \times 10^{-4}$ torr or better. The temperature within the furnace is then held at 1000° F. until the vacuum is allowed to recover to $9 \times 10^{-5}$ torr. This will be approximately one hour. After reaching the desired vacuum, the furnace is then heated 100° F. per minute to 1750° F. plus or minus 25° F., where it was held for at least ten minutes and preferably one hour. Care must be taken to hold the implant under the beta transus, in this case 1780° F., at all times. The implant is then quenched with pure dry argon to below 300° F. before exposing the implant to open air atmosphere.

During the course of the joinder compound melting, it will extract from the titanium balls and the titanium substrate sufficient titanium to create a bond between the various titanium alloy elements. This bond will be predominantly titanium which has been found to be in the range of 75%-95% by weight. The remainder of the bond includes from 1%-15% copper, 1%-15% nickel and 1%-10% indium, with substantially no impurities. It has been found that while some amounts of titanium may be allowed within the joining compound prior to heating, such titanium should be preferably kept below 5% of the compound, otherwise the compound itself may melt together rather than act to join various titanium parts together. The copper-nickel-indium compoound when in contact with titanium has been found to melt at temperatures as low as 1730° F., and yet give a bond greater than the strength of the bone which will grow within the pores created.

Holding the titanium alloy at a temperature near the beta transus, in addition to causing the bond to form, will also correspond with the first step in many hardening processes, such as solution treating or duplex annealing. After the implant has been quenched, the sample can be further treated to increase its hardness by such methods as precipitation hardening, heat treating, or age hardening. All these additional advantages obtained by maintaining the bonding process below the beta transus increases the strength of the implant. This allows its use as a replacement for cobalt steel in many areas of the body not currently allowed.

We claim:

1. A method for manufacture of titanium bone implant comprising the steps:
   (1) creating a titanium or titanium alloy bone implant substrate corresponding with bone matter to be replaced;
   (2) treating a portion of the substrate where the implant is to be joined with surrounding bone with a joinder compound comprising copper, nickel and indium, but including substantially no silver;
   (3) placing over said joinder compound pore creating means of titanium or titanium alloy;
   (4) heating the substrate, joinder compound and pore creating means to a temperature less than the beta transus of the titanium or titanium alloy being used until the joinder compound melts; and
   (5) cooling the substrate compound and pore creating means, creating a resultant, predominantly titanium, substantially uniform bond between the substrate and pore creating means.

2. The method of claim 1 wherein the joinder compound added is less than 2% by weight of the total implant weight.

3. The method of claim 1 wherein, after the substrate and pore creating means are cooled, the bone implant substrate is hardened.

4. The method of claim 1 wherein the substrate, joinder compound and pore creating means are held at a temperature just under the beta transus for at least ten minutes, and are then quenched.

5. The method of claim 4 wherein the quenching occurs by use of dry argon before exposure of the substrate and pore creating means to an open air atmosphere.

6. A method for manufacture of titanium bone implant comprising the steps:
   (1) creating a titanium or titanium alloy bone implant substrate corresponding with bone matter to be replaced;
   (2) treating a portion of the substrate where the implant is to be joined with surrounding bone with a joinder compound which has a chemical composition of 63%-66% copper, 30%-36% nickel, 3%-6% indium, 0-5% titanium and 0-1% iron and other impurities by weight;
   (3) placing over said joinder compound pore creating means of titanium or titanium alloy;
   (4) heating the substrate, joinder compound and pore creating means to a temperature less than the beta transus of the titanium or titanium alloy being used until the joinder compound melts; and
   (5) cooling the substrate compound and pore creating means, creating a resultant, predominantly titanium, substantially uniform bond between the substrate and pore creating means.

7. A method for manufacture of titanium bone implant comprising the steps:
   (1) creating a titanium or titanium alloy bone implant substrate corresponding with bone matter to be replaced;
   (2) treating a portion of the substrate where the implant is to be joined with surrounding bone with a joinder compound;
   (3) placing over said joinder compound pore creating means of titanium or titanium alloy;
   (4) heating the substrate, joinder compound and pore creating means to a temperature less than the beta transus of the titanium or titanium alloy being used until the joinder compound melts; and
   (5) cooling the substrate compound and pore creating means, creating a resultant, predominantly titanium, substantially uniform bond between the substrate and pore creating means which after the heating and cooling cycle is 75%-95% titanium, 1%-15% copper, 1%-15% nickel and 1%-10% indium by weight.

* * * * *